(12) United States Patent
Altrogge et al.

(10) Patent No.: US 9,080,139 B2
(45) Date of Patent: Jul. 14, 2015

(54) CONTAINER WITH A PLURALITY OF REACTION SPACES AND ELECTRODES

(75) Inventors: Ludger Altrogge, Mechernich (DE); Timo Gleissner, Euskirchen (DE); Andreas Heinze, Cologne (DE); Herbert Mueller-Hartmann, Cologne (DE); Andreas Wirth, Weidenberg (DE)

(73) Assignee: LONZA COLOGNE GMBH, Cologne (DE)

( * ) Notice: Subject to any disclaimer, the term of this patent is extended or adjusted under 35 U.S.C. 154(b) by 476 days.

(21) Appl. No.: 13/145,124

(22) PCT Filed: Jan. 20, 2010

(86) PCT No.: PCT/EP2010/000296
§ 371 (c)(1),
(2), (4) Date: Dec. 2, 2011

(87) PCT Pub. No.: WO2010/083986
PCT Pub. Date: Jul. 29, 2010

(65) Prior Publication Data
US 2012/0087841 A1    Apr. 12, 2012

Related U.S. Application Data

(60) Provisional application No. 61/146,228, filed on Jan. 21, 2009.

(30) Foreign Application Priority Data

Jan. 20, 2009  (EP) .................................. 09000700

(51) Int. Cl.
*C12M 1/32*    (2006.01)
*C12M 1/42*    (2006.01)

(52) U.S. Cl.
CPC ............... *C12M 23/12* (2013.01); *C12M 35/02* (2013.01)

(58) Field of Classification Search
CPC .............................. C12M 35/02; C12M 23/12
USPC ........................................................ 435/285.2
See application file for complete search history.

(56) References Cited

U.S. PATENT DOCUMENTS

| | | |
|---|---|---|
| 5,183,744 A | 2/1993 | Kawamura et al. |
| 6,352,853 B1 | 3/2002 | King et al. |
| 6,878,538 B1 | 4/2005 | Walters et al. |
| 2006/0087522 A1 | 4/2006 | Muller-Hartmann et al. |

(Continued)

FOREIGN PATENT DOCUMENTS

| | | |
|---|---|---|
| EP | 1 577 378 A1 | 9/2005 |
| WO | 02/05293 A2 | 1/2002 |

(Continued)

*Primary Examiner* — Nathan Bowers
*Assistant Examiner* — Gautam Prakash
(74) *Attorney, Agent, or Firm* — Joyce von Natzmer; Agris & von Natzmer LLP

(57) ABSTRACT

The invention relates to a container (1) with at least three reaction spaces (2) which in each case have at least one electrode pair for applying an electric voltage for generating an electric field within the reaction space (2) and which are arranged geometrically in at least one row and/or electrically connected in at least one row, wherein at least one electrode (3, 4) of a reaction space (2) is a common electrode (3, 4) with at least one other reaction space (2). According to the invention n+x electrodes (3, 4, 5) are provided, wherein n is the number of reaction spaces (2), with n≥3 and x is the number of rows, with x≥1.

15 Claims, 12 Drawing Sheets

(56) References Cited

U.S. PATENT DOCUMENTS

2007/0231873 A1 10/2007 Ragsdale
2008/0090287 A1* 4/2008 Larsen .................. 435/287.5
2008/0220493 A1 9/2008 Ragsdale et al.

FOREIGN PATENT DOCUMENTS

| WO | 2005/044983 A2 | 5/2005 |
| WO | 2007/094947 A2 | 8/2007 |
| WO | 2008109588 A2 | 9/2008 |

* cited by examiner

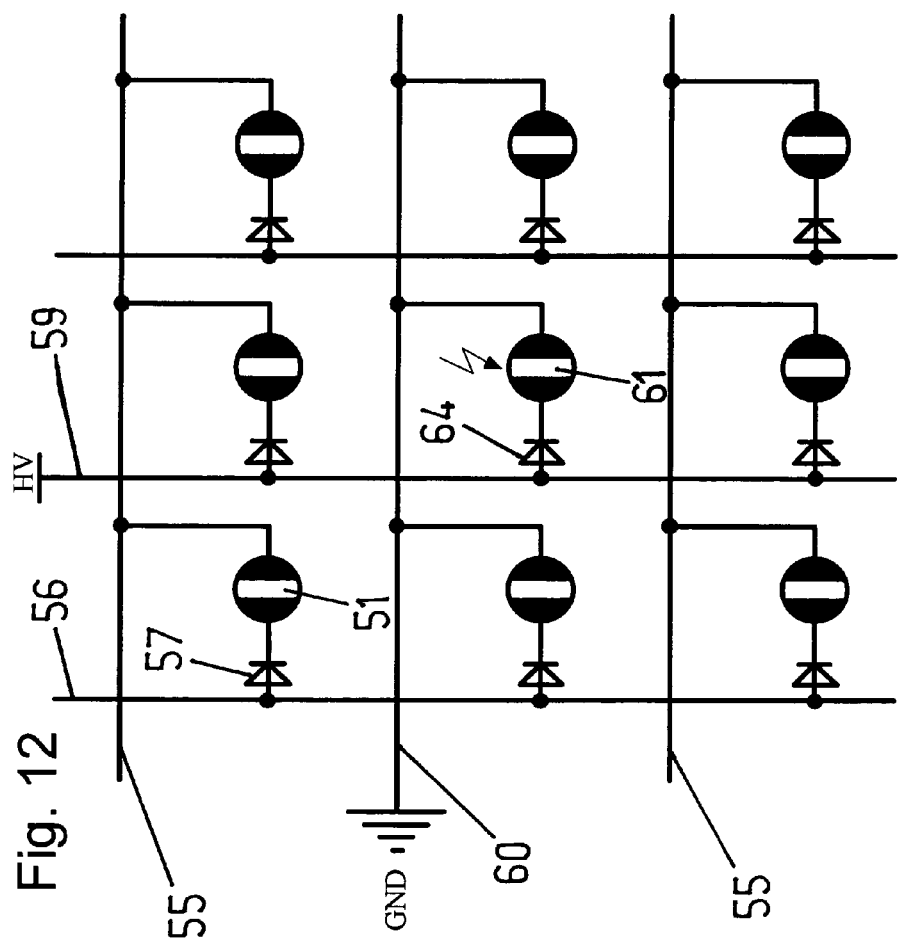

CONTAINER WITH A PLURALITY OF REACTION SPACES AND ELECTRODES

CROSS REFERENCE TO RELATED APPLICATIONS

This is the U.S. national stage of International application PCT/EP2010/000296, filed Jan. 20, 2010 designating the United States, claiming priority to European patent application no. EP 09000700.6, filed Jan. 20, 2009, and the benefit of U.S. provisional application No. U.S. 61/146,228, filed Jan. 21, 2009.

FIELD OF THE INVENTION

The invention relates to a container with at least three reaction spaces which in each case have at least one electrode pair for applying an electric voltage for generating an electric field within the reaction space and which are arranged geometrically in at least one row and/or electrically connected in at least one row, wherein at least one electrode of a reaction space is a common electrode with at least one other reaction space. The invention further relates to a lid for a container with at least two reaction spaces which in each case have at least one electrode for applying an electric voltage for generating an electric field within the reaction space and which are arranged geometrically in at least one row and/or electrically connected in at least one row, wherein the electrodes can be electrically contacted by means of contact points and the lid covers the reaction spaces. The invention also relates to a method for the production of the container mentioned, in which, per reaction space, at least two regions made from a conductive polymer are injected into an injection mould and a wall region made from a non-conductive polymer which delimits the reaction spaces is injected around the at least two regions.

BACKGROUND OF THE INVENTION

Containers provided with electrodes are particularly used in applications in which the reaction batch must be acted upon with an electric voltage pulse, such as for example electroporation, electrofusion and electrostimulation of living cells. Containers of this type can also have a plurality of reaction spaces, wherein each reaction space can be provided with electrodes. These containers are generally designated as multiwell plates, microtitre plates or multiwells. They are primarily used in biochemical and pharmaceutical applications, in which a multiplicity of reaction batches must be tested at the same time. In this case, the endeavour to provide a number of reaction spaces, for example 384, which is as large as possible, particularly in the case of HT analyses (HT=high throughput), is to be recognised, as here a multiplicity of samples should be tested in the shortest time possible.

The known containers usually consist of a plurality of reaction spaces which in each case have two electrodes which are in contact with the reaction batch, for example a cell suspension, in the reaction space. The two electrodes of a reaction space generate an electric field and a current flow when an electric voltage is applied in the interior of the reaction space, wherein they have different potentials and/or polarities in the case of direct current, for example. The electrodes with the same polarity, that is to say for example all cathodes and/or all anodes, of the different reaction spaces are in this case either constructed in one piece or electrically coupled to one another, so that they can be connected to the voltage source via a common electrical contact.

The loading of the reaction spaces of such containers with voltage pulses takes place by means of special switching arrangements which comprise one or two storage device(s) for storing electric charges. The storage devices are in each case capacitors which are charged to a predetermined electric charge and can output defined voltage pulses by means of targeted discharge. The storage devices are connected to electric switches, for example power semiconductors, by means of which the targeted discharge of the storage devices is switched. The use of two storage devices allows the output of two short voltage pulses that follow one another or merge into one another, which can be of advantage in the case of the electroporation of certain cell types. Contact pins are generally used for the electrical contacting of the electrodes of the containers, which contact pins are arranged on arms or plates and are manually or automatically brought into contact with the electrodes.

A container with a plurality of reaction spaces is known from EP-A-1 577 378, which container comprises a plurality of modules. Each module in this case has two rows of reaction spaces arranged in parallel, which reaction spaces in each case have an electrode pair, consisting of a first and a second electrode, for applying an electric voltage for generating an electric field within the reaction space. The first electrodes arranged on the same side of the different reaction spaces of a row are electrically conductively coupled, whilst the second electrodes of a reaction space can be electrically separately connected. In this case, the oppositely arranged first electrodes of different reaction spaces of adjacent rows are also electrically conductively coupled. In this known container, all reaction spaces are separately or individually addressable, that is to say each separate reaction space can be loaded with a voltage pulse independently of the other reaction spaces.

A container with a plurality of reaction spaces is further known from U.S. Pat. No. 5,183,744, in the case of which container the separate reaction spaces are likewise separately addressable. Each separate reaction space of this known container is provided with two electrodes, wherein in each case one of the electrodes of an electrode pair is electrically coupled to the corresponding electrodes of the other reaction spaces of a row of reaction spaces. The other electrode of the electrode pair in each case of a reaction space is separately electrically contacted, so that each separate reaction space can be individually loaded with a voltage pulse. U.S. Pat. No. 5,183,744 further discloses a container with a plurality of reaction spaces, in the case of which container the electrodes of the separate reaction spaces are connected to one another in the manner of a matrix. The matrix is in this case formed by conductor tracks which cross, wherein the conductor tracks are separated from one another at the respective crossing points by an insulating layer. The separate layers are connected via contact points to the conductor tracks so that each separate reaction space is theoretically addressable. Namely, if a voltage is applied to two crossing conductor tracks, then theoretically only the reaction space which is connected to these two conductor tracks is loaded with the voltage. It has been established in practice however that parasitic currents arise in the case of such a matrix, so that electric current also unintentionally flows through other reaction spaces. A solution of this type therefore has the disadvantage that undesired side effects occur, which significantly impair the efficiency and the reproducibility of the methods carried out with containers of this type.

WO 2005/044983 A2 likewise discloses a container with a plurality of reaction spaces, in the case of which container each reaction space has an electrode pair for applying an electric voltage. The electrodes are in this case, as already known from U.S. Pat. No. 5,183,744, connected to one another by means of crossing conductor tracks in the manner of a matrix. Here as well, parasitic currents and thus undesired side effects consequently cannot be prevented.

US 2007/0231873 A1 discloses a container with a plurality of reaction spaces, in the case of which container each separate reaction space is provided with two oppositely arranged electrodes. However, in the case of this container, the separate reaction spaces are not individually addressable, rather only separate groups which in each case consist of a plurality of reaction spaces, are simultaneously loaded with a voltage pulse.

A container with a plurality of reaction spaces is further known from WO 2007/094947 A2, in the case of which container each reaction space has two oppositely arranged electrodes. However, this known container also has the disadvantage that the separate reaction spaces are not individually addressable here, but rather merely addressable in groups.

All known containers have the disadvantage that either the reaction spaces are not separately addressable or the containers have a high number of electrodes overall, wherein the number of electrodes is twice as high as the number of reaction spaces. A reduced active and passive volume of the separate reaction spaces results from this in the case of the given dimensions of the container.

SUMMARY OF THE INVENTION

It is the object of the invention to provide a container with individually addressable reaction spaces of the type mentioned at the beginning, which container, at the given dimensions of the container, has an increased active and passive volume of the separate reaction spaces.

According to the invention, the object is achieved by a container of the type mentioned at the beginning, in which n+x electrodes are provided, wherein n is the number of reaction spaces, with $n \geq 3$ and x is the number of rows, with $x \geq 1$. The active volume of the separate reaction spaces at the given dimensions of the container are maximised by means of the reduction of the number of electrodes. The volume of a reaction space which is located between the electrodes, i.e. inside of which the actual reactions or processes essentially take place, is thus designated as an active volume in the sense of the invention. "Row" in the sense of the invention means that the reaction spaces are geometrically arranged in at least one row, line or column and/or the reaction spaces or at least one of their electrodes are switched electrically in at least one row. Thanks to the construction of the container according to the invention, the number of electrodes required for a container with 384 reaction spaces can for example be reduced from for example 768 to 408. Thanks to the reduced number of electrodes, material can further be saved and the outlay on apparatus on the sides of the voltage pulse generator and the contacting device can be reduced considerably. Furthermore, the outlay in the production of the mould is reduced in the case of the production of the container according to the invention in the injection moulding process.

In an advantageous configuration of the invention, it is provided that at least one common electrode is arranged at least partially between two adjacent reaction spaces within the row. Thanks to this alternating geometric arrangement of the electrodes, the distance between the electrodes or contact elements assigned to these is maximised, so that the electrical reliability can be markedly increased. In this case, the electrodes can also be arranged offset and/or in a zig zag manner with respect to the longitudinal axis of the container.

In an advantageous configuration of the invention, it is provided that the electrodes are provided with contact elements which can be electrically contacted for applying the electric voltage. Preferably, particularly the common electrode of the two reaction spaces is provided with a contact element. The electrodes are easy to contact by means of the contact elements, wherein a material can be chosen for the contact elements which ensures an optimal current flow into the electrodes. Each contact element of the container preferably has the greatest possible distance to the respective adjacent contact elements.

In a particularly advantageous configuration of the invention, it is provided that the contact elements with which the electrodes of a reaction space are provided are arranged on opposite sides of this reaction space. Preferably, the contact elements are in this case arranged diagonally oppositely and/or offset or in a zig zag manner with respect to the length of the container, so that they assume the largest possible spacing with respect to one another. In this manner, electrical sparkovers are prevented from occurring between two adjacent contact elements. Furthermore, the passive volume of the separate reaction spaces is thereby maximised in the case of the given overall volume. The volume of a reaction space which is not located between the electrodes, i.e. inside of which actually no reactions or electrically stimulated processes essentially take place, is thus designated as a passive volume in the sense of the invention. Preferably, the contact surface of the contact elements to the electrodes, which is located on or within the electrodes, has an area of at least 5 $mm^2$, preferably at least 6 $mm^2$, particularly preferably at least 7 $mm^2$, and in particular at least 8 $mm^2$.

The contact elements can, in an advantageous configuration of the invention, be partially enclosed by the electrodes, wherein at least 10%, particularly at least 20% or at least 30%, preferably at least 40% and particularly preferably at least 50%, of the length of the contact elements can lie within the electrodes.

Preferably, the contact elements are constructed in a pin shape, needle shape or screw shape and/or have an at least approximately round cross section. This shape of the contact elements simplifies the fixing of the contact elements in the electrodes and ensures an exceptional electrical contact in the case of the production of the containers according to the invention. The contact elements can for example be overmoulded by the conductive material of the electrodes in the injection moulding process or screwed into the conductive electrode material. For the further improvement of the electrical contact, the contact elements can also be knurled or roughened in some other manner. Also, cross sections which are at least flattened at least to some extent can be advantageous in certain cases, e.g. in order to improve the anchoring in the electrodes.

In an advantageous configuration of the invention, the reaction spaces in the upper region have an opening, wherein the electrodes in the upper region can be contacted. Thanks to the contacting from above, the underside of the container remains accessible, so that optical measurements can be carried out for example. Furthermore, in the case of this embodiment, the container can be cooled easily via the underside, particularly via the electrodes, which is of advantage on account of the strong heat generation, particularly in applications in which work is carried out with voltage pulses in rapid succession or with a high throughput and with a very high amplitude.

In a further advantageous configuration of the invention, it is provided that the contact elements are arranged on the upper side of the electrodes and/or project upwardly out of the electrodes, so that the electrodes can be easily contacted from above. This has the advantage that the bottom remains free and thus the transparency for analysis of the reaction space contents is possible. In the case that for specific applications a bottom other than the standard bottom is required, the bottom can, for example mechanically or chemically, be removed and replaced by a bottom made from another material (e.g. film or glass), without losing the functionality of the container according to the invention.

In a particularly advantageous configuration of the invention, it is provided that at least one, preferably each, row forms a module and that the modules can be directly or indirectly connected to one another. Thanks to this modular construction, it is possible to provide various formats of the container according to the invention very flexibly. Thus, for example by means of the provision of modules with 16 reaction spaces, containers with 96 reaction spaces, consisting of 6 modules, or containers with 384 reaction spaces, consisting of 24 modules, can be provided by means of the simple combination of the separate modules. Preferably, the separate modules are in this case fixed in a suitable frame, so that they are releasably or unreleasably connected to one another and form a unit. The assembly of the modules in the frame can for example take place by means of irreversible latching mechanismsor by means of adhesive bonding. The reversible assembly of the modules in the frame with corresponding latching mechanisms is likewise possible. The modules can also be fixed in the frame by means of ultrasonic welding, screwing, riveting, hot caulking or clamping. The modules preferably consist of two plastic components, i.e. for example electrically conductive polycarbonate and transparent polycarbonate, as well as insertion pins, which can for example consist of preferably nickel-plated brass. The conductive polycarbonate is used for producing the electrodes and the transparent polycarbonate as a basis for the base body or the wall region. The frame can be a plastic injection moulded part and consist of polystyrene or other thermoplastic plastics for example.

If the container and/or each reaction space has a bottom which is at least to some extent transparent, optical monitoring and/or measurements can be undertaken in the interior of the reaction spaces. In this case, the container and/or each reaction space can have a bottom which consists at least to some extent of glass and/or plastic.

In order to enable the adhesion of cells or to carry out certain optical measurements, the bottom can be coated at least to some extent. The coating can in this case comprise artificial polymers and/or biopolymers.

In a particular embodiment of the invention, the bottom can extend continuously under the entire container.

Preferably, the container according to the invention comprises a multiplicity of reaction spaces, preferably 6, 8, 12, 16, 24, 32, 48, 64, 96, 128, 192, 384, 1536, 3456 or 6144 reaction spaces.

At least one electrode of the container according to the invention can consist of a polymer which is doped with an electrically conductive material. All electrically conductive materials can be used as a dopant in this case, for example metals or conductive plastics. Particularly preferred are carbon-containing substances, particularly carbon fibres, graphite, carbon black and/or carbon nanotubes. The dopant is in this case contained in a concentration of from 20 to 80% by weight in the polymer.

The contact elements preferably consist of a contact material which at 23° C. has a lower specific resistance or interfacial resistance than that material of which the electrodes consist. The contact material can for example be a metal and/or have a specific resistance at 23° C. below $1 \times 10^{-5}$ Ohm·cm, preferably of $1 \times 10^{-6}$ to $2 \times 10^{-6}$ Ohm·cm.

If the electrodes of the container according to the invention should or must be cooled from below, it is particularly advantageous if the electrodes project downwardly beyond the bottom of the container and/or the wall region of the reaction spaces. In this manner, the contact to a suitable cooling element can be intensified so that the heat transfer can be optimised.

The invention also relates to a lid of the type mentioned at the beginning, which is in particular provided for the container according to the invention and which has a number of holes which corresponds to the number of contact points. Thanks to this configuration according to the invention, the electrodes can be contacted without having to remove the lid. The protective function of the lid therefore also remains intact during the carrying out of the respective method.

In a particularly advantageous configuration of the invention, it is provided that the lid has n+x holes, wherein n is the number of the reaction spaces, with n≥3 and x is the number of rows, with x≥1.

In a further advantageous configuration of the invention, it is provided that at its side facing the reaction spaces in the region of the edges of the reaction spaces, the lid has elevations and/or is provided with sealing material, so that no material or no liquid can escape from the separate reaction spaces. That is particularly advantageous if very high currents flow through the reaction spaces and increased gas formation thereby arises, which can lead to sputtering. Thanks to the particular configuration of the lid on the inside, cross contaminations, that is to say contaminations from one reaction space to another reaction space, in particular can therefore be avoided.

The lid can be a plastic injection moulded part and consist of transparent polystyrene for example.

The container according to the invention is produced in a method of the type mentioned at the beginning, in which initially the contact elements are inserted into the injection mould and are then overmoulded by at least one of the two polymers. In this manner, the container can be produced with high quality and precision in an injection moulding process at high speed. The polymer, with which the contact elements are overmoulded, is in this case preferably the electrically conductive polymer. The two polymers, of which the container essentially consists, can also be injection moulded in multi-component injection moulding. In this case, the two polymers are however not injected as a mixture, but rather in two steps of an operation which follow one another. Thanks to the insertion of the contact elements into the injection mould, the necessity of an additional operation is in this case avoided and thus the production method is simplified and accelerated.

The injection moulding process for the production of microtitre plates is an advantageous method for producing the same in high piece numbers. The use of insertion pieces in injection moulded parts serves to improve or enable mechanical or electrical properties of injection moulded parts. It offers a cost-effective option, as the contact elements in an operation can automatically be inserted into the injection mould. This simplifies the production of multiwell plates for electroporation and this process is additionally connected with high precision.

Alternatively to the overmoulding of the contact elements, the latter can also be screwed or pressed into the conductive electrode material. It is further possible to adhesively bond the contact elements into the conductive electrode material with a conductive adhesive.

In a further advantageous embodiment, the electrodes can be shaped in such a manner that they can be provided on the upper side of the container by means of hot stamping with contact elements or contact surfaces.

The container according to the invention can according to the invention also be produced in a method in the case of which separate modules are produced in the injection moulding process, which modules in each case consist of reaction spaces arranged in at least one row and have fixing elements at their narrow sides. In this case, at least one module can be fixed in a frame element, wherein the frame element for each module to be fixed has at least one fixing means, preferably in the form of a prolongation, in each case on two opposite sides, which fixing means corresponds to the respective fixing element, preferably in the form of eyelets. Preferably, the module is fixed in the frame element by means of hot caulking, wherein the fixing means engages into the respective fixing element when the module is inserted into the frame element, and wherein the fixing means is heated in such a manner that positive connection results between the fixing means and the fixing element. Alternatively, the modules could also be fixed in the frame element by means of ultrasonic welding or adhesively bonded into the frame element by means of a suitable adhesive, however.

In a preferred embodiment of the method according to the invention, the bottom of the wall region can be removed from the container and a new bottom can subsequently be attached to the container. In this manner, the container can be flexibly adapted to particular requirements. If the new bottom consists of transparent material, a container can for example be provided, in the case of which optical measurements can be carried out in the interiors.

The invention further relates to a container with at least one reaction space which has at least one electrode for applying an electric voltage for generating an electric field within the reaction space. In order to be able to individually identify the container, according to the invention it is unreleasably connected to at least one transponder, particularly a transponder for the unambiguous identification of the container. In this case, the data relating to the respective container can be read and electronically processed by means of a suitable reader device. A time consuming manual marking or labelling of the containers is avoided in this manner, wherein according to the invention the information no longer has to be optically recognisable. This is particularly advantageous if, in a test series, a multiplicity of containers is used, as is the case in the case of high throughput processes for example. With the aid of the container according to the invention, processes of this type can be accelerated, wherein the data capture is improved and above all becomes more reliable. Furthermore, the information is more difficult to manipulate, the process reliability is markedly increased and the traceability of the containers is optimal.

In an advantageous configuration of the invention, the transponder is integrated into the wall region which delimits or forms the at least one reaction space. If the wall region or base body of the container consists of an injection-mouldable plastic, the transponder can for example be injected into the wall region of the container during the production process.

The transponder is preferably an RFID transponder. Alternatively, it can also be a "one wire identification" tag such as e.g. "iButton" (MAXIM/DALLAS). The RFID transponder preferably comprises an antenna, an analogue circuit, a digital circuit and/or a storage device.

According to the invention, a container of this type can be produced in a process in which the container is produced in the injection moulding process and the transponder is overmoulded by at least one polymer.

Each container can according to the invention therefore be equipped with a transponder (tag) which is fixed in or on the container either as a glass capsule during the injection moulding process or subsequently by means of gluing in place or depositing in the form of a label. The device in which the containers are processed should have a corresponding technology for reading the transponder. In the device, a storing of the identification then follows at processing time. By means of the information read, an error in the plate sequence can, in accordance with the previously configured experiment, occur by means of adaption of the setup at runtime. The stored information can be used for the evaluation/correlation of error patterns and assignment to production batches. In the case of reusing already processed containers, the experiment can accordingly be stopped or a warning can be output to the user. The container according to the invention and equipped with a transponder can further be used for sequence testing, tracing reaction plates, ensuring process reliability or defect avoidance in the case of the electric treatment for the analysis of liquid samples.

The problems indicated at the beginning in the case of the known containers with matrix-like coupling of the electrodes are solved by a container according to the invention with at least four reaction spaces, in the case of which the reaction spaces in each case have at least one electrode pair, consisting of a first and a second electrode, for applying an electric voltage to the electrodes of the reaction space, wherein at least two groups of coupled electrodes are formed in that in each case at least two first electrodes of different reaction spaces are electrically coupled and wherein at least two further groups of coupled electrodes are formed in that the second electrodes of the different reaction spaces in each case are likewise electrically coupled, wherein each group of coupled electrodes contains a different group of reaction spaces and two groups of coupled electrodes in each case contain at most one common reaction space. According to the invention, the first electrodes of different reaction spaces are, in an advantageous manner, connected to one another at least via diodes, wherein at least one diode is assigned to each reaction space. The diodes in this case prevent parasitic currents from being able to spread from the intentionally addressed reaction space which is loaded with the voltage pulse into other, non-addressed reaction spaces. Undesired side effects, which could impair the efficiency and/or reproducibility of the respective method are thereby effectively avoided.

In this case, it is particularly advantageous if the diodes are arranged in the direction of the respective reaction space in the reverse direction. Alternatively, however, the diodes can be arranged on every side of the respective reaction space in every direction as long as their arrangement and orientation within the container as a whole according to the invention is such that no parasitic currents can flow through non-addressed reaction spaces. The diodes can therefore also be arranged in the direction of the respective reaction space in the forward direction.

In an advantageous configuration of the invention, it is provided that the electrodes of different reaction spaces are coupled by means of at least one common electrically conductive connecting element, preferably a conductor track. In this case, the diodes are preferably arranged between the electrically conductive connecting element and the first electrode of the respective reaction space.

The container according to the invention can comprise a multiplicity of reaction spaces, preferably 6, 8, 12, 16, 24, 32, 48, 64, 96, 128, 192, 384, 1536, 3456 or 6144 reaction spaces can be provided.

The invention is explained by way of example in the following on the basis of the figures.

BRIEF DESCRIPTION OF THE DRAWINGS

FIG. 12 shows an alternative circuit diagram of the electrodes, the conductor tracks and the diodes of a container according to the invention with matrix-like coupling of the electrodes.

DETAILED DESCRIPTION OF VARIOUS AND PREFERRED EMBODIMENTS

Figure 1:
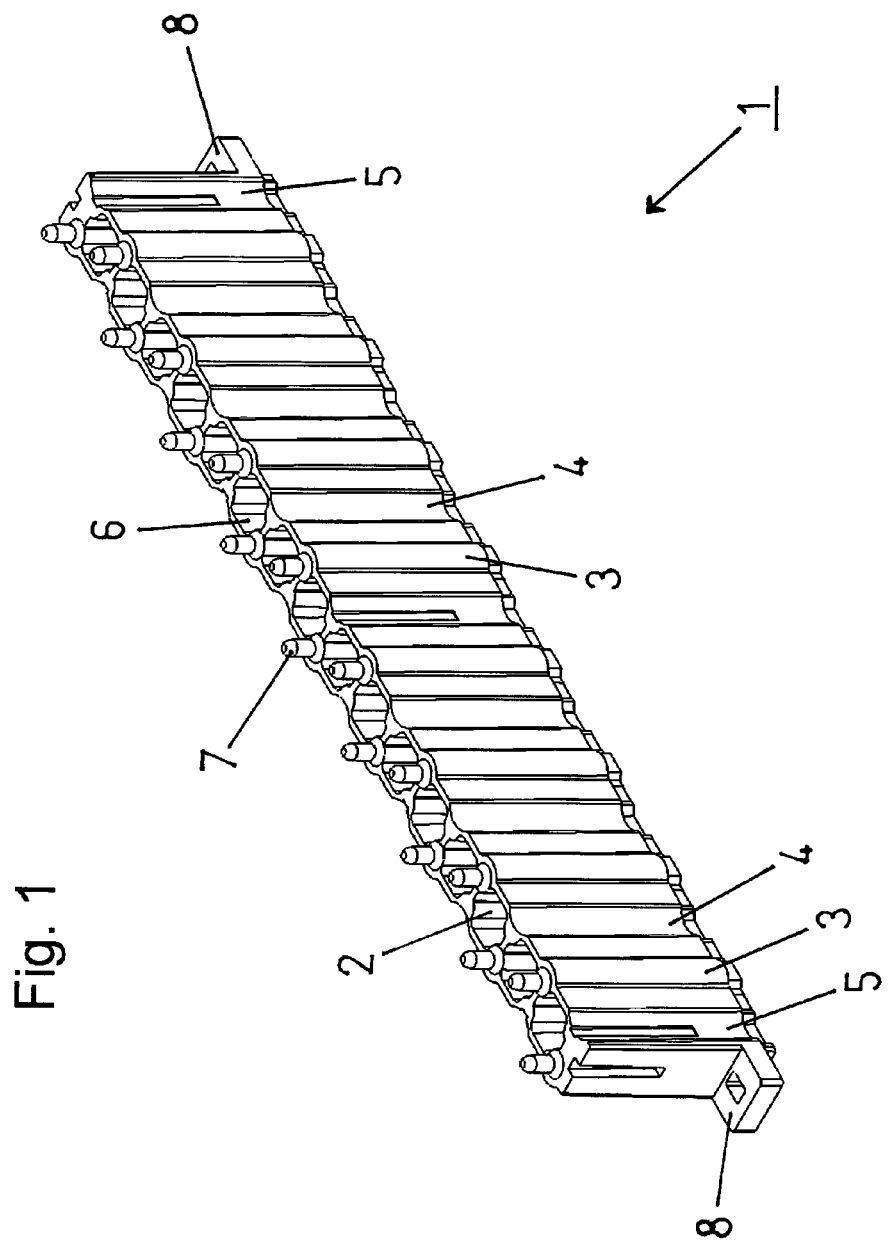
FIG. 1 shows a perspective view of a particularly advantageous embodiment of a container according to the invention.

FIG. 1 shows a perspective view of a particularly advantageous embodiment of a container according to the invention. The container 1 comprises 16 reaction spaces 2, which in the present example are arranged in a row (x=1) directly next to one another. Each reaction space 2 has two oppositely arranged electrodes 3, 4, 5, the shape and arrangement of which is explained on the basis of FIG. 3. The electrodes 3, 4 arranged in each case between two reaction spaces 2 are common electrodes 3, 4, that is to say these electrodes 3, 4 are connected with the interiors 6 of the two adjacent reaction spaces 2. The fact that each electrode 3, 4 arranged between two reaction spaces 2 is a common electrode 3, 4 means that the container 1 according to the invention in the present exemplary embodiment comprises 17 electrodes in total. In addition to the common electrodes 3, 4, a separate electrode 5 is in each case arranged on the outer ends of the container 1. The container 1 according to the invention therefore comprises 16 reaction spaces 2 (n=16) and 17 electrodes 3, 4, 5 (n+x=17). If each reaction space were provided with a separate electrode pair, then a corresponding container with 16 reaction spaces would comprise 32 electrodes. Thanks to the solution according to the invention, the container 1 according to the invention comprises only 17 electrodes 3, 4, 5 however, so that the number of electrodes in the present exemplary embodiment could be reduced by 15 electrodes. In the present exemplary embodiment, each electrode 3, 4, 5 is provided with a contact element 7, which enables the electrical contacting of the electrodes. The contact elements 7 in the present exemplary embodiment are metal pins which are overmoulded with the electrode material. The contact elements 7 project upwardly out of the container 1, so that the electrodes 3, 4, 5 can be contacted from above. This has the advantage that the underside of the container 1 remains free, so that the underside of the container 1 is accessible for example for optical measurements. The container 1 according to the invention can either be used as a separate container or else be used as a module within a module arrangement. If the container 1 according to the invention is used as a module, then it can be fixed in a frame element by means of the fixing elements 8 which in each case are formed on the narrow sides of the container 1. In this manner, a plurality of containers can be combined with one another so that overall, a container with a multiplicity of reaction spaces, for example 96 or 384 reaction spaces, can be provided.

Figure 2:
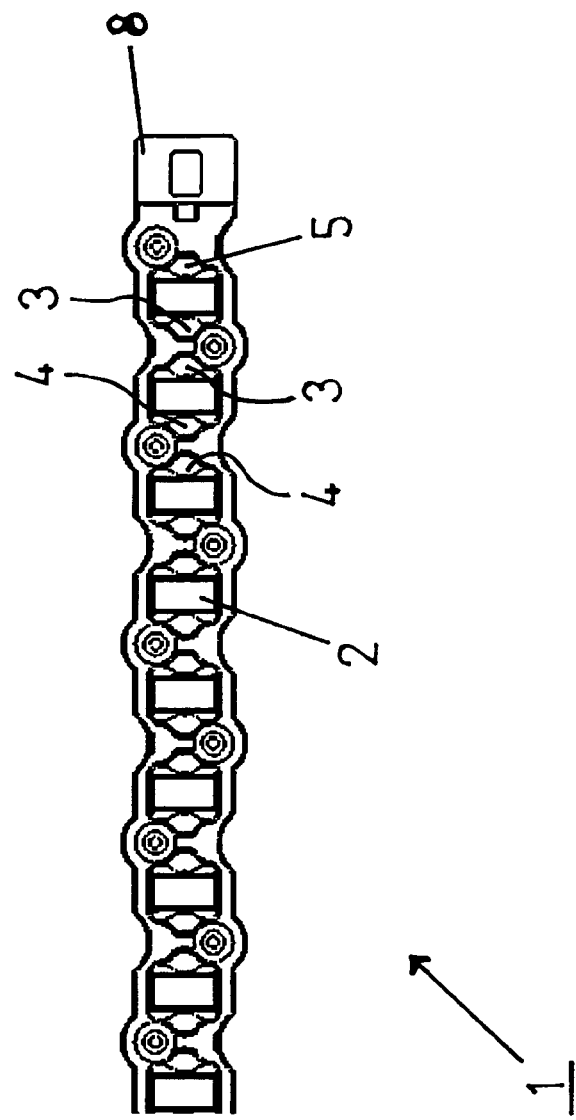
FIG. 2 shows a plan view onto the container according to the invention in accordance with FIG. 1.

FIG. 2 shows a plan view onto the container 1 according to the invention in accordance with FIG. 1. It becomes clear in this illustration that the electrodes 3, 4 arranged in each case between two reaction spaces 2 represent common electrodes 3, 4 for the two adjacent reaction spaces 2. Thanks to this arrangement, the container 1 according to the invention can be constructed in a very compact manner, wherein the number of electrodes 3, 4, 5 or the number of the contact elements 7 is markedly reduced. It further becomes clear here that the contact elements 7 are arranged in an offset manner, that is to say extend in a zig zag manner over the length of the container 1, so that they assume the largest possible spacing with respect to one another. Thanks to the maximisation of the distance of the contact elements to one another, it is achieved that the likelihood of electrical sparkovers between two contact elements is minimised and/or the maximum allowable pulse voltage increases.

Figure 3:
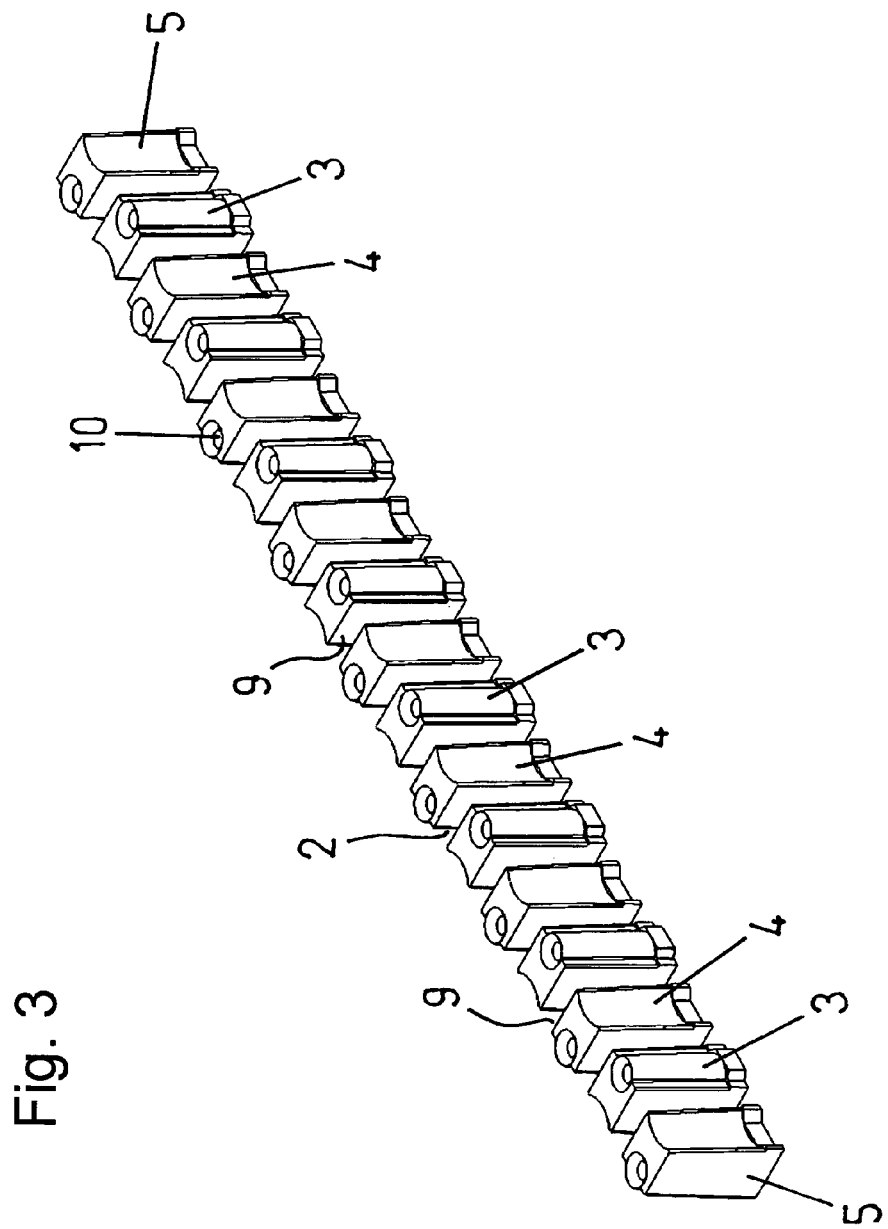
FIG. 3 shows a perspective view of the arrangement of the electrodes of the container according to FIG. 1.

FIG. 3 shows a perspective view of the arrangement of the electrodes 3, 4, 5 of the container 1 according to FIGS. 1 and 2. The electrodes 3, 4, 5 are arranged in a row, wherein the surfaces 9, which in each case face one another, of adjacent electrodes 3, 4, 5 form a reaction space 2 lying between them, through which reaction space an electric current can flow in the case of the application of an electric voltage to the electrodes 3, 4, 5. The surfaces 9 of the electrodes 3, 4, 5 which form the respective reaction space 2 are constructed in a flat manner and in each case arranged approximately, that is to say within the limits of production tolerances, in a plane-parallel manner. The electrodes consist of an electrically conductive material, preferably of a polymer which is doped with an electrically conductive material. Electrodes made from injection mouldable polymer, for example polycarbonate which is doped with carbon fibres and/or graphite, are particularly preferred. The electrodes are preferably injected into a suitable injection mould in the injection moulding process. In this case, the electrodes are, preferably after the injection moulding of a further polymer, preferably transparent polycarbonate, injection moulded into the injection mould in one operation around contact elements, for example metal pins which were inserted into the injection mould in the regions 10 which have remained free in this illustration.

Figure 4:
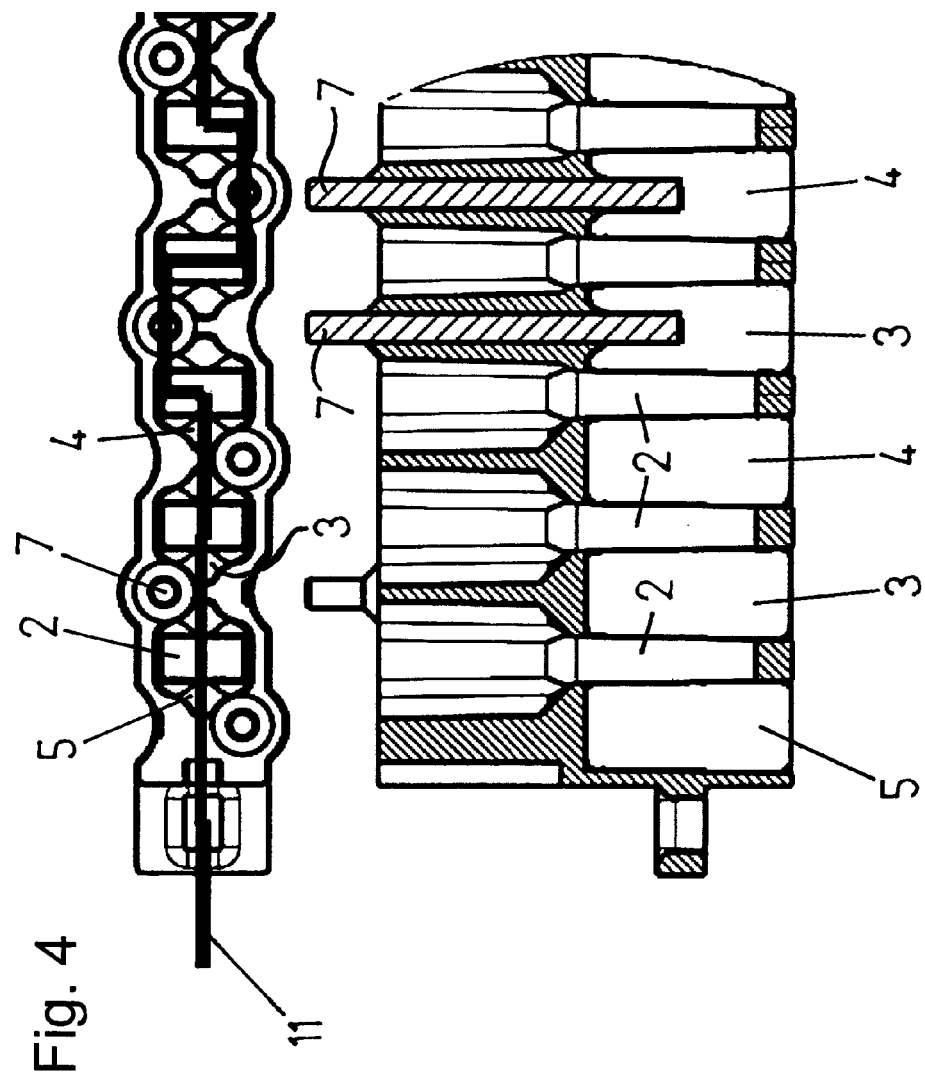
FIG. 4 shows a cross section, as well as the shape of the section through a part of the container according to the invention in accordance with FIG. 1.

FIG. 4 shows a cross section through a part of the container 1 according to the invention in accordance with the FIGS. 1 and 2, wherein the upper illustration clarifies the path of the cut using the section line 11. It once again becomes clear here that the common electrodes 3, 4 are in each case arranged between the reaction spaces 2. The electrodes 3, 4, 5 (shown in white) in this case preferably consist of a conductive polymer, for example polycarbonate which is doped with carbon fibres and graphite. The remaining regions of the container 1

(shown shaded here) preferably likewise consist of a polymer, preferably of transparent polycarbonate. The contact elements 7 are injected into the two polymers and project upwardly out of the container 1, so that the electrodes 3, 4, 5 can be contacted from above. The contact elements 7 are constructed in a pin-shaped manner and preferably have a round cross section. At least 10%, preferably 50-60%, of the length of the contact elements 7 should be embedded into the polymers. The contact surface of the contact elements 7 within the conductive polymer should preferably comprise at least 5 mm$^2$, preferably 6-8 mm$^2$.

Figure 5:
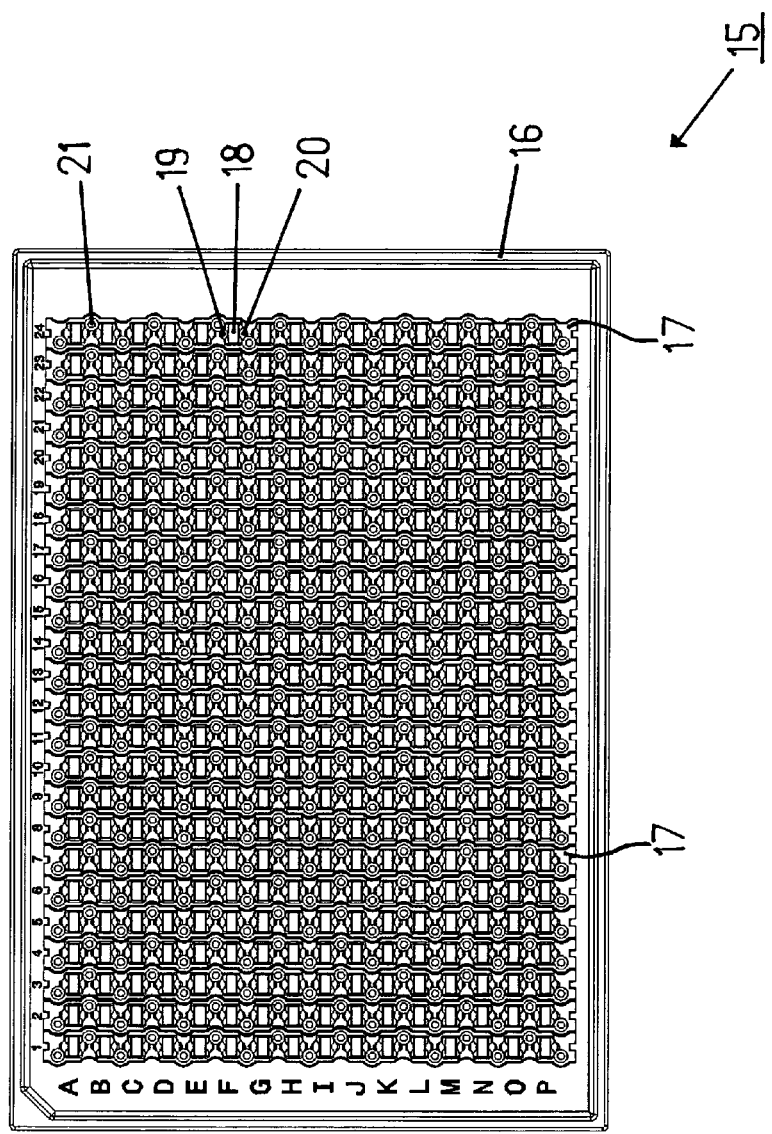
FIG. 5 shows a plan view onto a particular embodiment of a container according to the invention composed of modules and with a frame element.

FIG. 5 shows a plan view onto a particular embodiment of a container according to the invention. The container 15 consists of a frame element 16, in which 24 modules 17 are fixed. Each module 17 comprises 16 reaction spaces 18, which in each case are arranged in a row. In total, the container 15 therefore comprises 384 reaction spaces 18. The modules 17 in this case correspond to the container 1 according to FIG. 1, that is to say each reaction space 18 has two electrodes 19, 20, which in each case are provided with a contact element 21 which projects upwards out of the container 15. The container 15 according to the invention is particularly suitable for electrotransfections in the high throughput method (high throughput screening).

Figure 6:
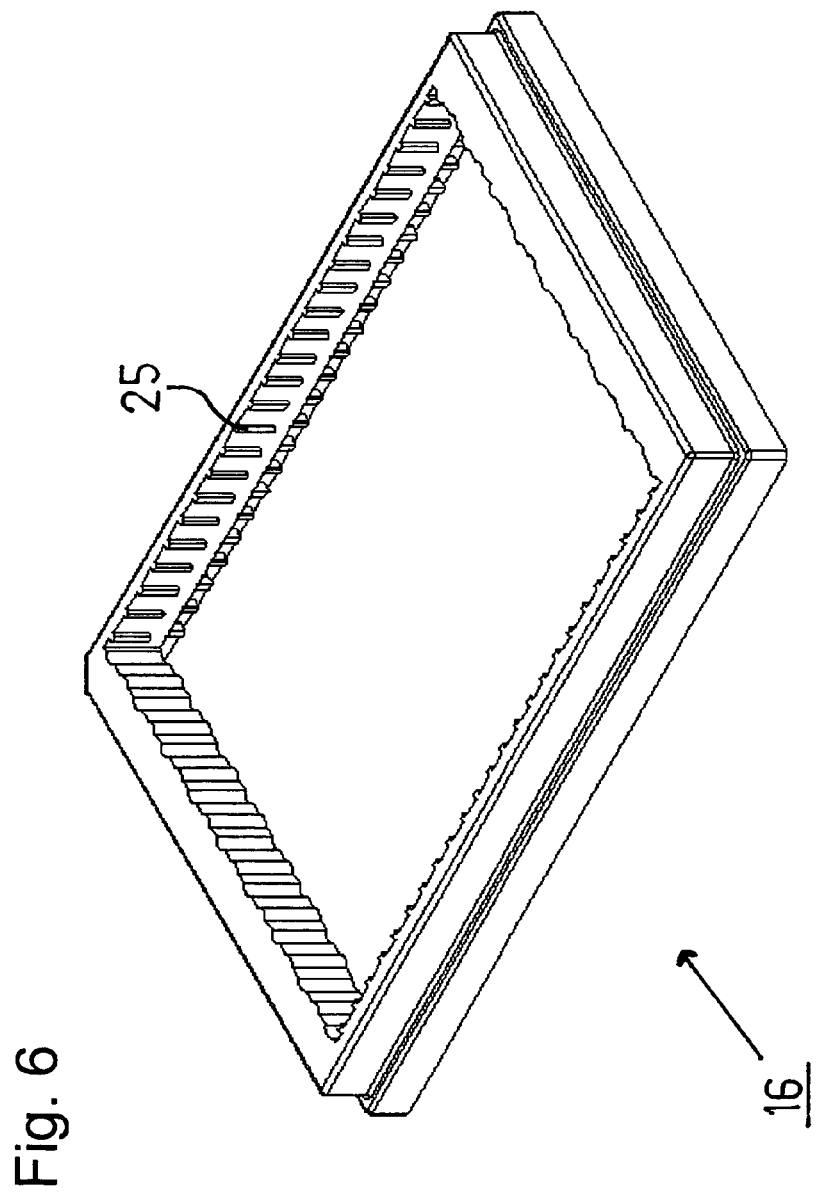
FIG. 6 shows a perspective view of the frame element according to FIG. 5 without modules.

FIG. 6 shows a perspective view of the frame element 16 according to FIG. 5 without modules. The frame element 16 is a plastic injection moulded part which preferably consists of polystyrene. The insides of the longitudinal sides of the frame element 16 have guide means 25 which are used for the guiding or centring of the modules 17 according to FIG. 5. The modules can for example be fixed in the frame element 16 by means of hot caulking. To this end, frame elements must be produced in injection moulding which have one plastic pin on each side per module to be fixed. The modules in turn have eyelets on both narrow sides, which eyelets are adapted to the size of the plastic pins. Thus, one can insert the modules into the frame. The pins are then heated by means of a suitable tool and a positive connection between pin and eyelet results.

Figure 7:
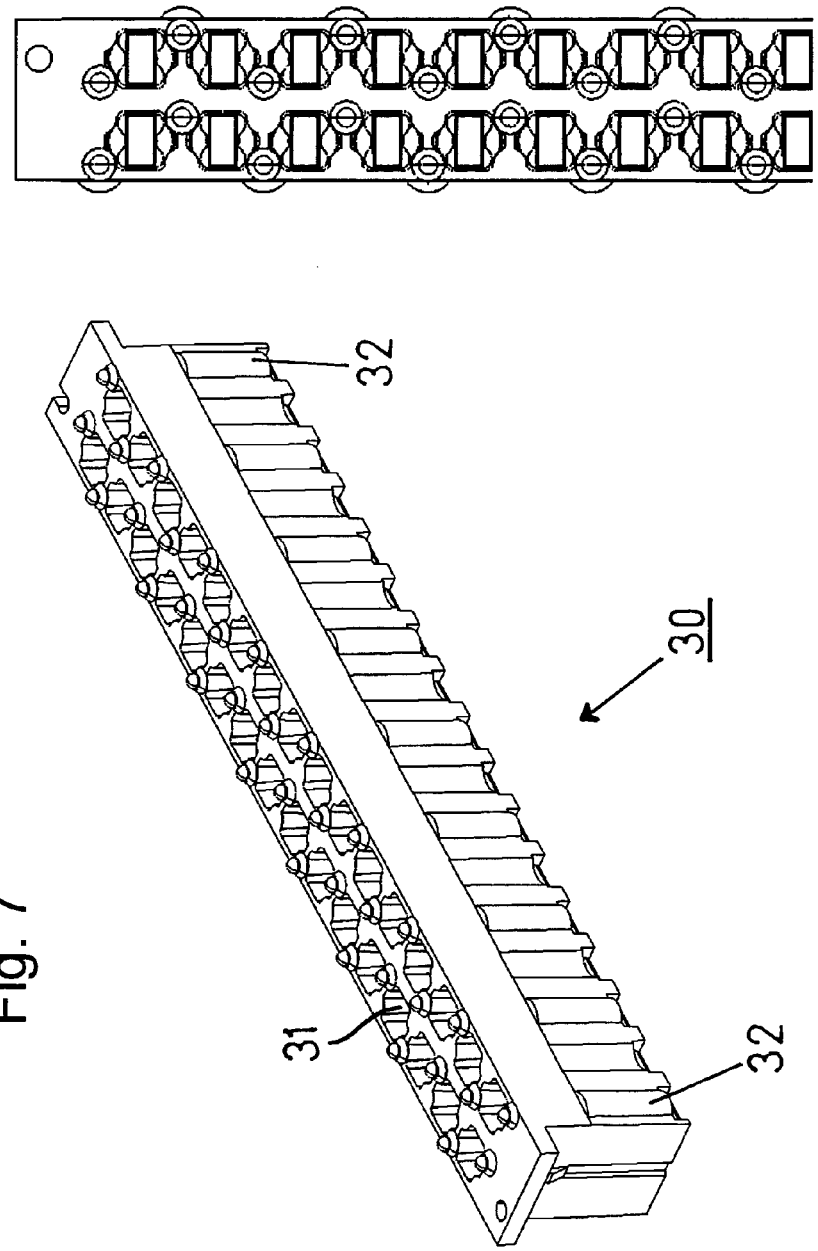
FIG. 7 shows a perspective view of a further particularly advantageous embodiment of a container according to the invention.

FIG. 7 shows a perspective view of a further particularly advantageous embodiment of a container according to the invention. The container 30 essentially corresponds in its construction to the container 1 according to FIG. 1. In contrast to the container 1 according to FIG. 1, the container 30 comprises two rows (x=2) of reaction spaces 31. Each row in this case comprises sixteen reaction spaces 31, so that the container 30 comprises 32 reaction spaces (n=32) in total. Each row of the container 30 comprises seventeen electrodes, so that the container 30 comprises 34 electrodes 32 (n+x=34) in total. If each reaction space were provided with a separate electrode pair, then a corresponding container with 32 reaction spaces would comprise 64 electrodes. Thanks to the solution according to the invention, the container 30 according to the invention comprises merely 34 electrodes 32 however, so that the number of electrodes in the present exemplary embodiment is reduced by 15 electrodes. In this manner, the active reaction space volumes can be maximised in the case of the given size.

Figure 8:
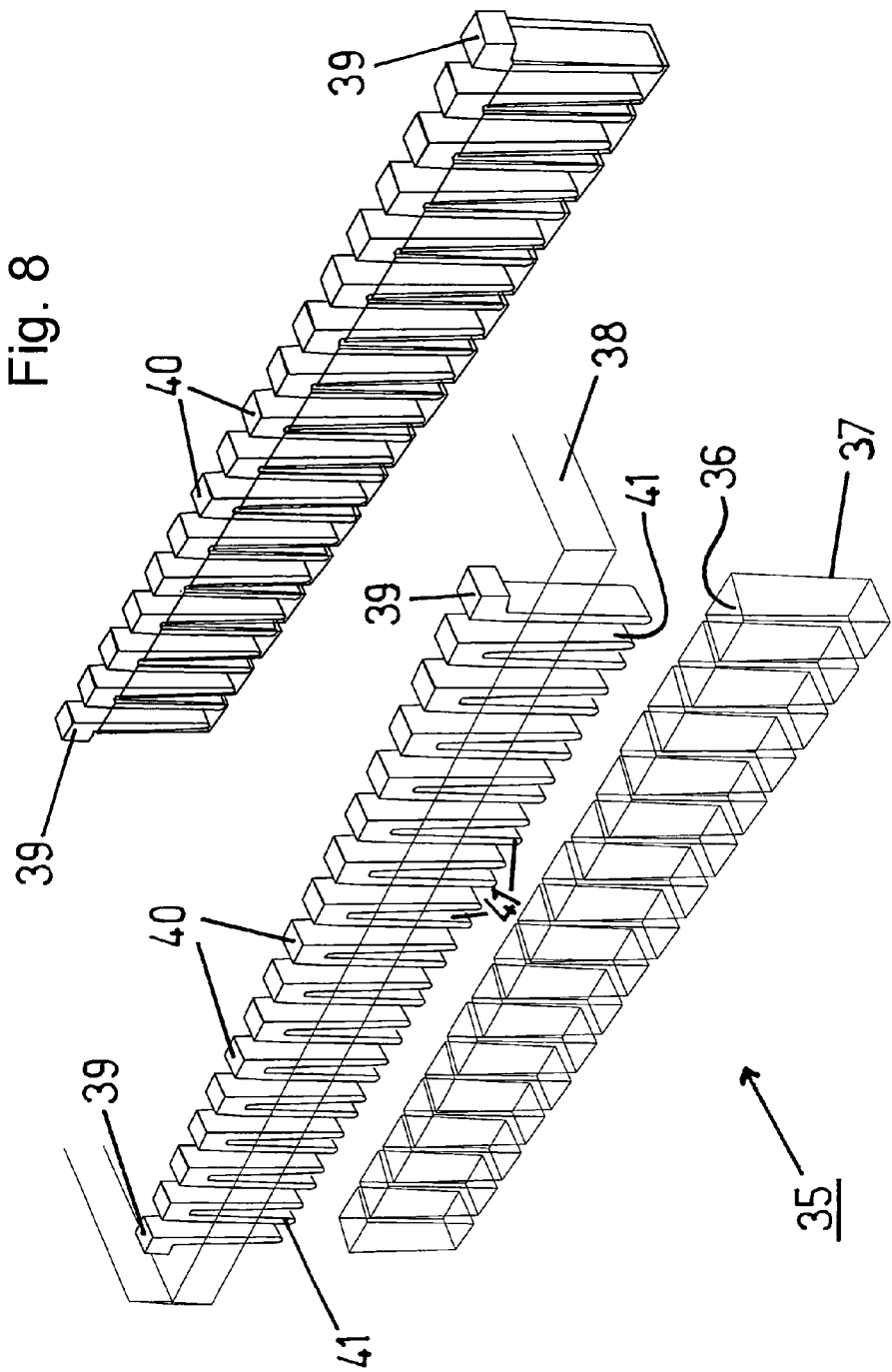
FIG. 8 schematically shows a perspective view of a further embodiment of a container according to the invention.

FIG. 8 schematically shows a perspective view of a further embodiment of a container according to the invention. The container 35 according to the invention comprises a plurality of rows of reaction spaces, of which only one row is shown here. The reaction spaces 36 are in each case formed by a wall region 37 which does not have any electrodes. The container 35 further comprises a lid 38, to the inside facing the reaction spaces 36 of which the electrodes 39, 40 are fixed. When attaching the lid 38 onto the wall regions 37 of the reaction spaces 36, the electrodes 39, 40 dip into the respective reaction spaces 36. When applying an electric voltage to the electrodes 39, 40, electric current can then flow through the reaction spaces 36. The electrodes 39 arranged at both ends of a row in each case are separate electrodes which in each case only dip into one reaction space 36. The electrodes 40 lying between them are by contrast common electrodes which in each case have two leg-like prolongations 41. In each case, one of the leg-like prolongations 41 of adjacent electrodes 40 in each case dips into a common reaction space 36, whilst the two leg-like prolongations 41 of each electrode 40 dip into in each case adjacent reaction spaces 36 (see illustration top right, without lid). In this manner, the electrodes 40 in each case form a common electrode for two adjacent reaction spaces 36. Each reaction space 36 consequently comprises an electrode pair which either consists of two leg-like prolongations 41 of two electrodes 40 or a leg-like prolongation 41 of one electrode 40 and a leg-like prolongation 41 of a separate electrode 39. A row (x=1) of the container 35 according to the invention with 16 reaction spaces 36 (n=16) is depicted in this illustration. The container 35 further comprises 17 electrodes 39, 40 (n+x=16 +1=17) and thus has a markedly reduced electrode number with respect to already known containers.

Figure 9:
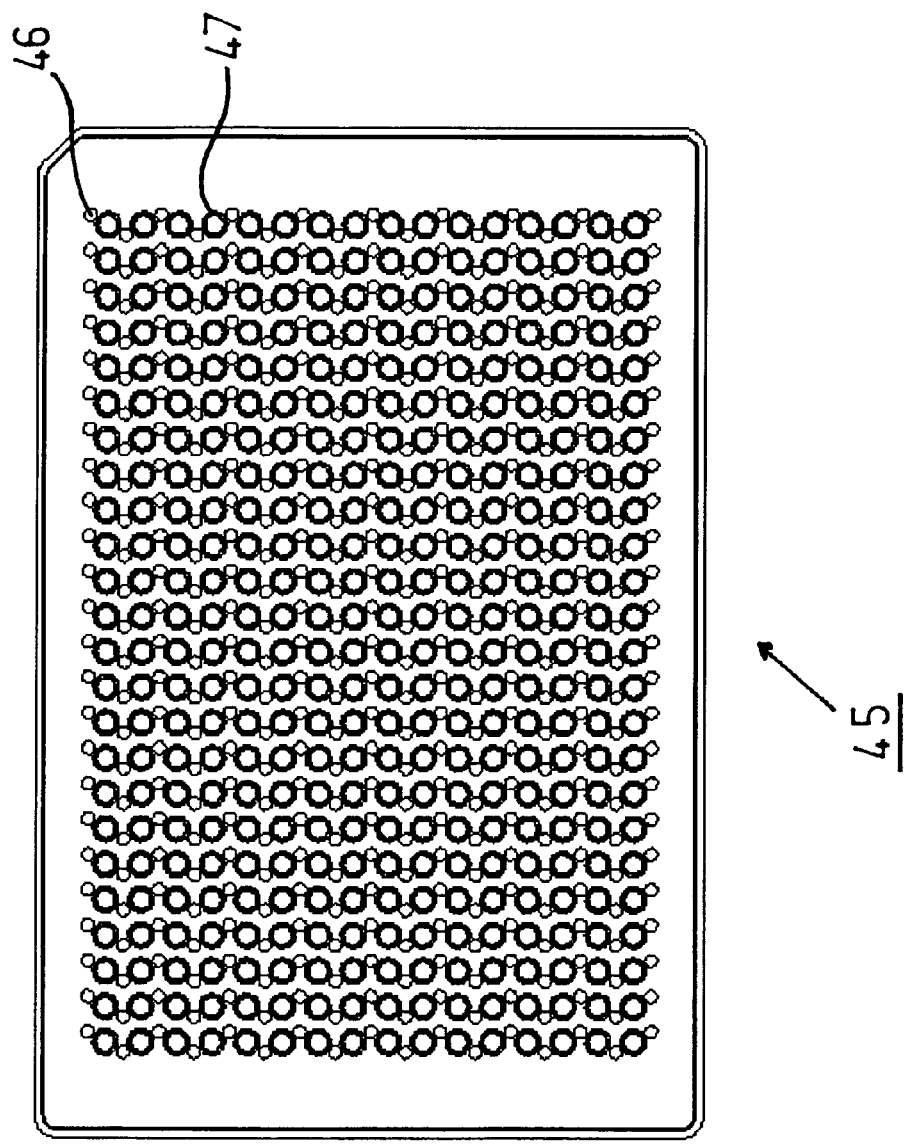
FIG. 9 shows a plan view onto the underside of a particularly advantageous embodiment of a lid according to the invention.

FIG. 9 shows a plan view onto the underside of a particularly advantageous embodiment of a lid according to the invention. The lid 45 can for example be used for covering the reaction spaces of the container 15 according to the invention in accordance with FIG. 5. The lid 45 has a number of holes 46 corresponding to the number of contact elements, through which holes the contact elements can be contacted. The lid has circular sealing rings 47 on its underside, which faces the container, which sealing rings seal the reaction spaces of the container with the lid 45 in place. In this manner, cross contaminations due to sputtering of the cell suspension located in the reaction spaces can be prevented. Instead of the sealing rings 47, simple elevations or beads can also be provided as long as the latter can seal the reaction spaces with respect to one another.

Figure 10:
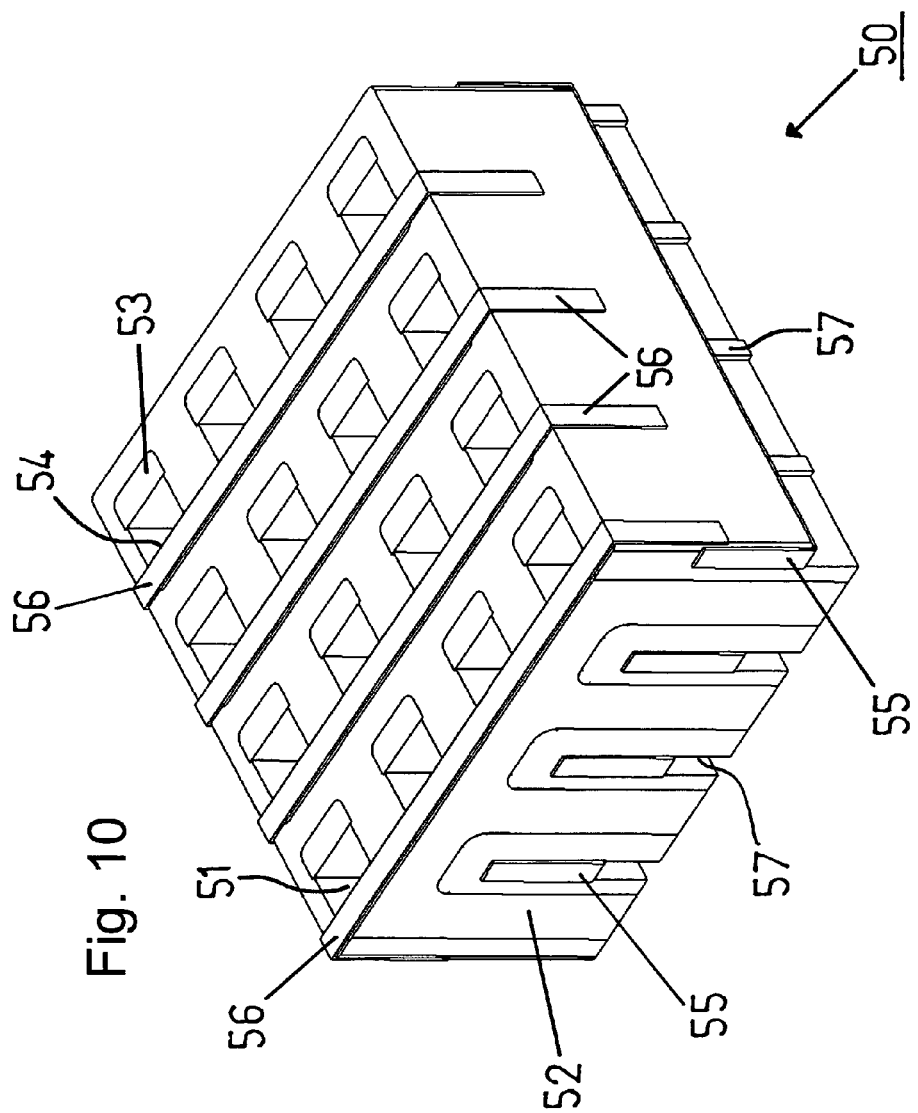
FIG. 10 shows a perspective view of a particularly advantageous embodiment of a container according to the invention with matrix-like coupling of the electrodes.

FIG. 10 shows a perspective view of a particularly advantageous embodiment of a container according to the invention with matrix-like coupling of the electrodes. The container 50 according to the invention comprises 16 reaction spaces 51 which are arranged in four rows overall in a base body 52. Each reaction space 51 is provided with two oppositely arranged electrodes 53, 54. The electrodes 53, 54 of a row are in each case electrically coupled to one another by means of connecting elements 55, 56 which cross in different planes. The connecting elements 55, 56 can be metallic conductor tracks for example which are connected to the separate electrodes. Preferably, the connecting elements are metal foils which are applied onto the electrodes by means of hot stamping. The first electrodes 53 in each case of a row of reaction spaces 51 are in this case electrically coupled by means of the connecting elements 55. The second electrodes 54 in each case of the rows of reaction spaces 51 arranged perpendicularly hereto are in each case coupled to one another by means of the connecting elements 56. The first electrodes 53 of the reaction spaces 51 are in this case connected to the connecting element 55 by means of diodes 57 in each case. The fact that each reaction space 51 is provided with a diode 57 means that all first electrodes 53 of the reaction spaces 51 are connected to one another by means of a diode 57 in each case. The diodes 57 are in this case preferably arranged in the direction of the respective reaction space 51 in the reverse direction. Thanks to the matrix-like coupling of the electrodes 53, 54, each reaction space 51 can, during the application of an electric voltage, be loaded separately with a voltage pulse or be addressed separately, depending on the connecting elements 55, 56 to which the voltage is applied. In this case, only the reaction space 51 which is located at the crossing point of the conductor tracks 55, 56 to which the voltage was applied is loaded with a voltage pulse in each case, which is explained with reference to FIG. 11. The diodes 57 in this case advantageously prevent parasitic currents from spreading from the reaction space 51 which is loaded with the voltage pulse via the conductor tracks 55 into other reaction spaces 51. Undesired side effects, which could impair the efficiency and/or reproducibility of the respective method are thereby avoided.

Figure 11:
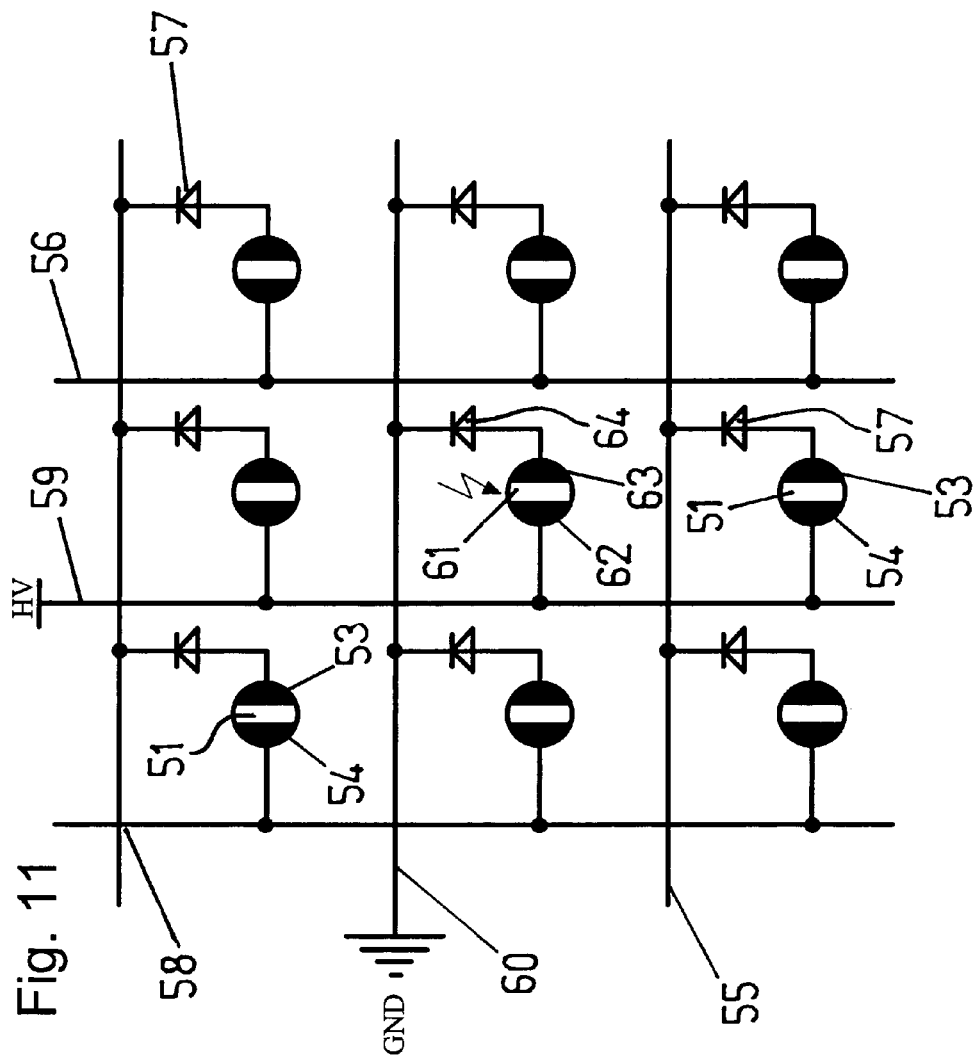
FIG. 11 shows a circuit diagram of a part of the container according to the invention in accordance with FIG. 10.

FIG. 11 shows a circuit diagram of the electrodes 53, 54, the conductor tracks 55, 56 and the diodes 57 of the container 50 according to the invention in accordance with FIG. 10. In this illustration, it becomes clear that the conductor tracks 55 form various groups of coupled first electrodes 53, whilst the conductor tracks 56 form various groups of the coupled second electrodes 54. The conductor tracks 55, 56 in this case run perpendicularly to one another, so that they form a matrix-like grid. The conductor tracks 55, 56 run in different planes, however, so that they are not electrically coupled to one another at the respective crossing points 58. Thanks to the conductor tracks 55, the first electrodes 53 of the rows of different reaction spaces 51 in each case are therefore electrically coupled. By means of the conductor tracks 56, the second electrodes 54 of the rows running perpendicularly hereto are electrically coupled to different reaction spaces 51. In the present illustration, three groups of coupled first electrodes 53 and three groups of coupled second electrodes 54 are therefore illustrated. Each group of coupled electrodes 53, 54 in this case comprises a different group of reaction spaces 51, wherein two groups of coupled electrodes 53, 54 in each case contain at most one common reaction space 51. It is therefore only through this reaction space 51 that an electric current flows in the case of the application of an electric voltage to the two groups of coupled electrodes 53, 54. Therefore, in the present exemplary embodiment, an electric voltage is applied to the conductor tracks 59 and 60 (HV=high voltage, GND=earth), so an electric current only flows through the addressed reaction space 61 (lightning symbol). In this case, the electric current flows from the conductor track 59 via the second electrode 62 through the reaction space 61 and then via the first electrode 63 and the diode 64 into the earthed conductor track 60. As, in the illustration shown, the inactive conductor track 55 does not constitute a sink, that is to say is not connected to earth (GND), although high voltage (HV) is applied at the second electrode 54 of the middle reaction space 51 in the lowest row, no current can flow. The diodes 57 at the first electrodes 53 of the "horizontal" neighbouring reaction spaces of the active reaction space 61 prevent the current flow from the current carrying diode 64 into inactive reaction spaces 51. Undesired side effects can thus effectively be prevented.

FIG. 12 shows an alternative circuit diagram of the electrodes, the conductor tracks and the diodes of a container according to the invention with matrix-like coupling of the electrodes. In contrast to the circuit diagram according to FIG. 11, the diodes 57, 64 are here arranged on the opposite side of the reaction spaces 51, 61, that is to say between the reaction spaces 51, 61 and the conductor tracks 56, 59. The diodes 57, 64 are therefore arranged in the direction of the conductor tracks 56, 59 in the reverse direction in this embodiment. Even in the case of this embodiment, the flow of parasitic currents into non-addressed reaction spaces can be avoided.

REFERENCE LIST

1 Container
2 Reaction space
3 Electrode
4 Electrode
5 Electrode
6 Interior
7 Contact element
8 Fixing element
9 Surface
10 Regions
11 Section line
15 Container
16 Frame element
17 Module
18 Reaction space
19 Electrode
20 Electrode
21 Contact element
25 Guide means
30 Container
31 Reaction space
32 Electrode
35 Container
36 Reaction space
37 Wall region
38 Lid
39 Electrode
40 Electrode
41 Prolongation
45 Lid
46 Holes
47 Sealing ring
50 Container
51 Reaction space
52 Base body
53 Electrode
54 Electrode
55 Connecting element, conductor track
56 Connecting element, conductor track
57 Diode
58 Crossing point
59 Conductor track
60 Conductor track
61 Reaction space
62 Electrode
63 Electrode
64 Diode

The invention claimed is:

1. Container comprising:
at least three reaction spaces which are arranged in at least one row in each case have at least one electrode pair for applying an electric voltage for generating an electric field within one reaction space of said reaction spaces and said electrodes being arranged in said at least one row, wherein at least one electrode of said one reaction space is a common electrode (a) of said one reaction space and (b) at least one other reaction space of said at least three reaction spaces and is arranged between (a) and (b), wherein n+x electrodes are provided, and wherein n is the number of reaction spaces with n ≥3 and x is the number of rows, with x≥1.

2. Container according to claim 1, wherein the at least one common electrode arranged between (a) and (b) has a first surface facing (a) and a second surface, which is arranged opposite the first surface, facing (b).

3. Container according to claim 1, wherein the electrodes are provided with contact elements which can be electrically contacted for applying electric voltage.

4. Container according to claim 3, wherein the common electrode of the two reaction spaces is provided with a contact element.

5. Container according to claim 3, wherein the contact elements of the container are arranged diagonally oppositely or offset to each other, or in a zig-zag manner with respect to the length of the container.

6. Container according to claim 3, wherein the contact elements with which the electrodes of a reaction space are provided, are arranged on opposite sides of this reaction space.

7. Container according to claim 3, wherein the contact surface of the contact elements to the electrodes which is located on or within the electrodes, has an area of at least 5 mm$^2$.

8. Container according to claim 3, wherein the contact elements are partially enclosed by the electrodes, wherein at least 40% of the length of the contact elements lies within the electrodes.

9. Container according to claim 3, wherein the contact elements are constructed in a pin shape, needle shape or screw shape.

10. Container according to claim 1, wherein the reaction spaces each have a bottom at an underside and an opening in an upper region, wherein the electrodes can be contacted in the upper region.

11. Container according to claim 3, wherein the contact elements are arranged on the upper side of the electrodes and project upwardly out of the electrodes.

12. Lid for a container according to claim 1, wherein the electrodes of the container can be electrically contacted via contact points and the lid covers the reaction spaces of the container wherein the lid has n+x holes, and wherein n is the number of the reaction spaces, with n≥3 and x is the number of rows, with x≥1.

13. Lid according to claim 12, wherein at its side facing the reaction spaces in an edge region of the reaction spaces, the lid has elevations.

14. Container according to claim 1, wherein the container is unreleasably connected to at least one transponder.

15. Container according to claim 14, wherein the at least one reaction space is delimited by a wall region into which the transponder is integrated.

* * * * *